United States Patent
Peng et al.

(10) Patent No.: US 8,039,250 B2
(45) Date of Patent: Oct. 18, 2011

(54) PIEZOELECTRIC-BASED NANOPORE DEVICE FOR THE ACTIVE CONTROL OF THE MOTION OF POLYMERS THROUGH THE SAME

(75) Inventors: Hongbo Peng, Yorktown Heights, NY (US); Gustavo A. Stolovitzky, Riverdale, NY (US); Stephen M. Rossnagel, Pleasantville, NY (US); Stanislav Polonsky, Putnam Valley, NY (US); Binquan Luan, Ossining, NY (US); Glenn J. Martyna, Croton-on-Hudson, NY (US)

(73) Assignee: International Business Machines Corporation, Armonk, NY (US)

( * ) Notice: Subject to any disclaimer, the term of this patent is extended or adjusted under 35 U.S.C. 154(b) by 29 days.

(21) Appl. No.: 12/723,724

(22) Filed: Mar. 15, 2010

(65) Prior Publication Data
US 2011/0223652 A1   Sep. 15, 2011

(51) Int. Cl.
*C12M 1/34* (2006.01)
*C12M 3/00* (2006.01)
(52) U.S. Cl. .................. 435/287.2; 435/6
(58) Field of Classification Search ........... 435/6, 287.2; 257/9; 204/628
See application file for complete search history.

(56) References Cited

U.S. PATENT DOCUMENTS

| | | | |
|---|---|---|---|
| 4,692,992 A | 9/1987 | Hsu | |
| 5,671,086 A | 9/1997 | Parvin et al. | |
| 6,180,490 B1 | 1/2001 | Vassiliev et al. | |
| 6,217,872 B1 | 4/2001 | Okayama et al. | |
| 6,413,792 B1 | 7/2002 | Sauer et al. | |
| 7,282,130 B2 | 10/2007 | Flory | |
| 7,347,921 B2 | 3/2008 | Barth et al. | |
| 7,468,271 B2 * | 12/2008 | Golovchenko et al. | .... 435/287.2 |
| 7,540,717 B2 | 6/2009 | Sheng et al. | |
| 2005/0101100 A1 | 5/2005 | Kretchmer et al. | |
| 2005/0110990 A1 | 5/2005 | Koo et al. | |
| 2005/0158763 A1 | 7/2005 | Ivanisevic et al. | |

(Continued)

FOREIGN PATENT DOCUMENTS
WO   WO2006122317   11/2006

(Continued)

OTHER PUBLICATIONS

Amit Meller et al., "Rapid nanopore discrimination between single polynucleotide molecules," PNAS, Feb. 1, 2000, vol. 97, No. 3, pp. 1079-1084.

(Continued)

*Primary Examiner* — Michael Marcheschi
*Assistant Examiner* — Shanta G Doe
(74) *Attorney, Agent, or Firm* — Cantor Colburn LLP; Vazken Alexanian

(57) ABSTRACT

Apparatus, system, and methods are provided for utilizing piezoelectric material for controlling a polymer through a nanopore. A reservoir is formed filled with conductive fluid. A membrane is formed that separates the reservoir. A nanopore is formed through the membrane. The membrane comprises electrical conductive layers, piezoelectric layers, and insulating layers. The piezoelectric layers are operative to control a size of the nanopore for clamping/releasing a polymer as well as to control the thickness of part of the membrane when a voltage is applied to the piezoelectric layers. Combinations of clamping/releasing the polymer and changing the thickness of part of the membrane can move a polymer through the nanopore at any electrically controlled speed and also stretch or break a polymer in the nanopore.

25 Claims, 17 Drawing Sheets

U.S. PATENT DOCUMENTS

| | | | |
|---|---|---|---|
| 2006/0105553 | A1 | 5/2006 | Wellhausen |
| 2006/0154399 | A1 | 7/2006 | Sauer et al. |
| 2006/0169588 | A1 | 8/2006 | Jacobson et al. |
| 2006/0180469 | A1 | 8/2006 | Han et al. |
| 2006/0246497 | A1 | 11/2006 | Huang et al. |
| 2007/0020146 | A1* | 1/2007 | Young et al. ............... 422/82.01 |
| 2007/0048745 | A1 | 3/2007 | Joyce et al. |
| 2007/0138132 | A1* | 6/2007 | Barth ............................... 216/56 |
| 2007/0190542 | A1 | 8/2007 | Ling et al. |
| 2008/0032290 | A1 | 2/2008 | Young |
| 2008/0102504 | A1 | 5/2008 | Akeson et al. |
| 2008/0119366 | A1 | 5/2008 | Sauer et al. |
| 2008/0171316 | A1 | 7/2008 | Golovchenko et al. |
| 2008/0257859 | A1 | 10/2008 | Golovchenko et al. |
| 2009/0136958 | A1 | 5/2009 | Gershow et al. |
| 2009/0221443 | A1 | 9/2009 | Heller et al. |
| 2009/0222216 | A1 | 9/2009 | Hibbs et al. |
| 2010/0025249 | A1 | 2/2010 | Polonsky et al. |
| 2010/0084276 | A1* | 4/2010 | Lindsay ........................... 205/93 |
| 2010/0327255 | A1* | 12/2010 | Peng et al. ......................... 257/9 |

FOREIGN PATENT DOCUMENTS

| | | |
|---|---|---|
| WO | WO2008051308 A2 | 5/2008 |
| WO | WO2008132643 A1 | 11/2008 |
| WO | WO2009032756 A2 | 3/2009 |

OTHER PUBLICATIONS

Akeson, Mark, et al., "Microsecond Time-Scale Discrimination Among Polycytidylic Acid, Polyadenylic Acid, and Polyuridylic Acid as Homopolymers or as Segments Within Single RNA Molecules," Biophysical Journal, vol. 77, Dec. 1999, pp. 3227-3233.

Branton, Daniel, et al., "The potential and challenges of nanopore sequencing" NIH Public Access—Author Manuscript, Nat Biotechnol. available in PMC May 18, 2009, pp. 1-17.

Gracheva, Maria E. et al., "Simulation of the electric response of DNA translocation through a semiconductor nanopore—capacitor", Institute of Physics Publishing, Nanotechnology, vol. 17 (2006), pp. 622-633.

Heng, Jiunn B. et al., "Sizing DNA Using a Nanometer-Diameter Pore", Biophysical Journal, vol. 87, Oct. 2004, pp. 2905-2911.

Kasianowicz, John J., et al., "Characterization of individual polynucleotide molecules using a membrane channel", Proc. Natl. Acad. Sci. USA, vol. 93, Nov. 1996, pp. 13770-13773.

Lagerqvist, Johan et al., "Fast DNA Sequencing via Transverse Electronic Transport", Nano Lett., vol. 6, No. 4, Received Jan. 17, 2006; revised Manuscript Received Mar. 1, 2006, pp. 779-782.

Soni, Gautam V. et al., "Progress toward Ultrafast DNA Sequencing Using Solid-State Nanopores", Clinical Chemistry, vol. 53, No. 11, (2007), pp. 1-6.

Polonsky et al., "Nanopore in metal-dielectric sandwich for DNA position control," Applied Physics Letters 91, 153103 (2007).

Douville, et al., "DNA Linearization Through Confinement in Nanofluidic Channels, Anal Bioanal Chem.", Aug. 2008; vol. 391; No. 7; pp. 2395-2409; Abstract; p. 2402, col. 2; para 5; p. 2406; col. 2; para 2; p. 2407; Fig. 5b.

International Search Report—PCT; Notification of Transmittal of The International Search Report and The Written Opinion of the International Searching Authority, or the Declaration; Apr. 5, 2011; International application No. PCT/US1123872.

United States Patent and Trademark Office, Non-Final Office Action for U.S. Appl. No. 12/704,665 received Mar. 16, 2011; pp. 1-15.

Written Opinion of the International Searching Authority; date of mailing Apr. 5, 2011; pp. 1-6; International application No. PCT/US11/23872.

* cited by examiner

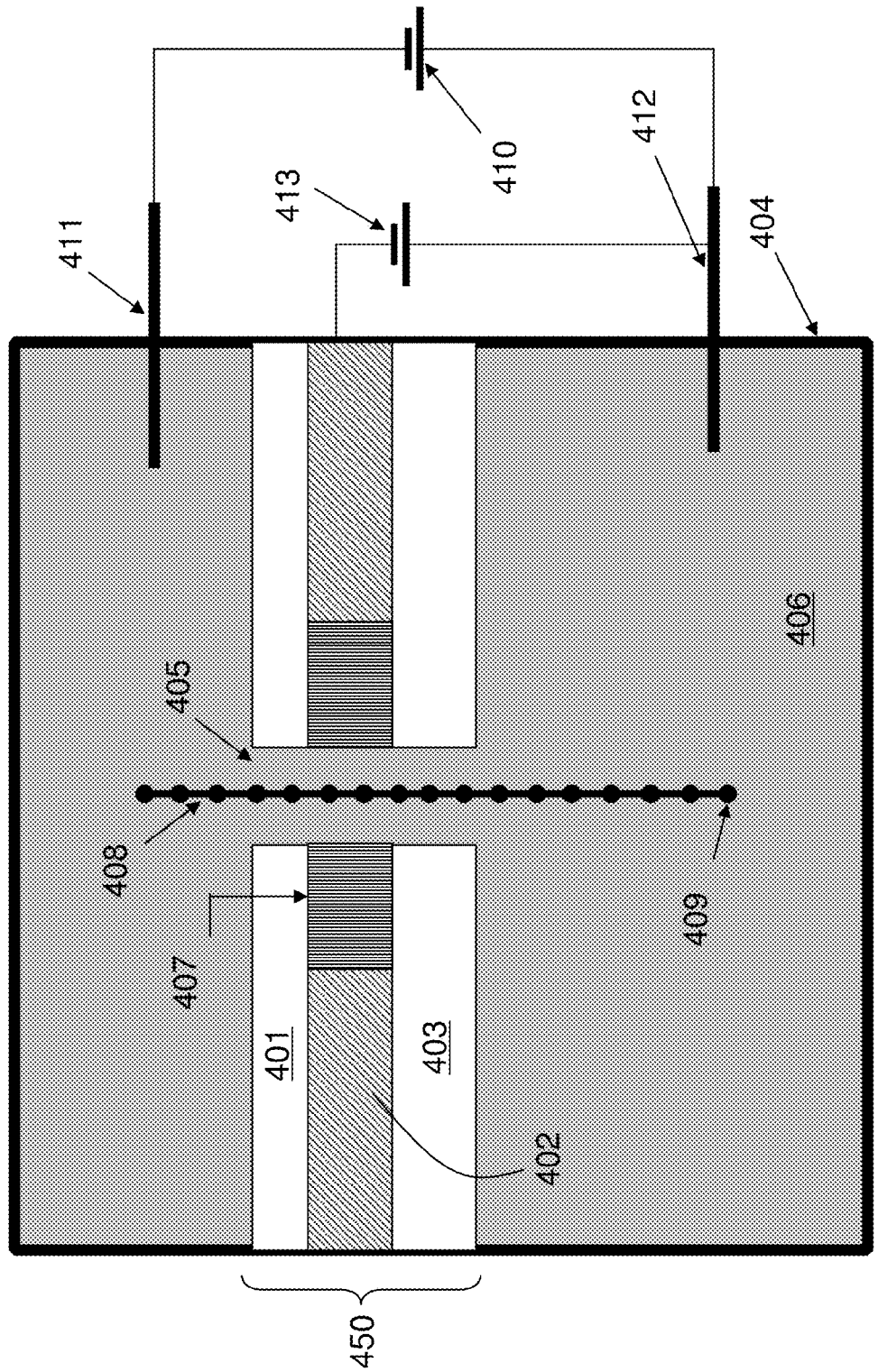

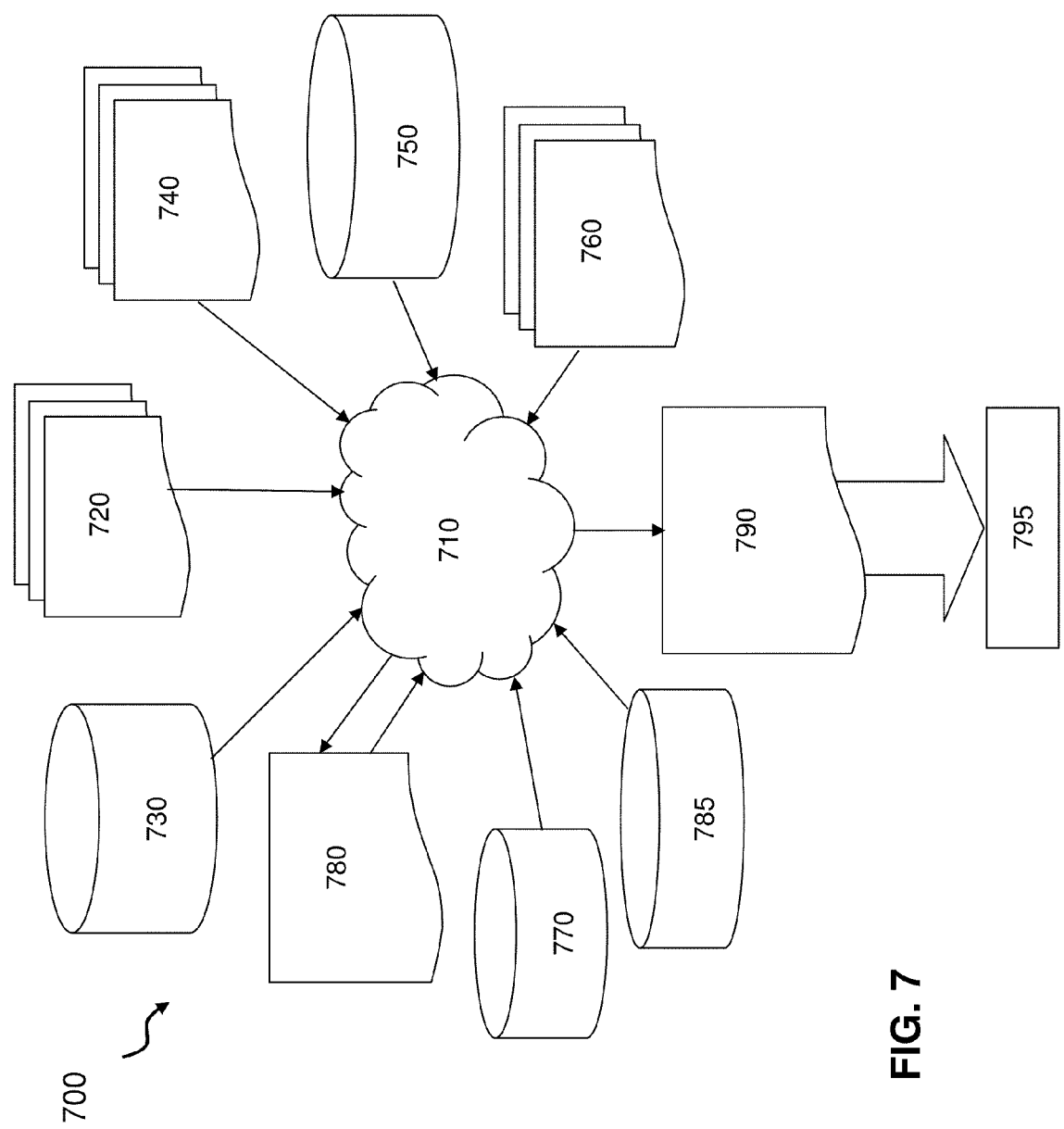

PIEZOELECTRIC-BASED NANOPORE DEVICE FOR THE ACTIVE CONTROL OF THE MOTION OF POLYMERS THROUGH THE SAME

This application contains subject matter which is related to the subject matter of the following co-pending application, which is assigned to the same assignee as this application: International Business Machines Corporation of Armonk, N.Y.; and the below listed application is incorporated herein by reference in its entirety: NANOPORE BASED DEVICE FOR CUTTING LONG DNA MOLECULES INTO FRAGMENTS, filed Mar. 15, 2010, application Ser. No. 12/723,842.

BACKGROUND

Exemplary embodiments relate to nanodevices, and more specifically, to piezoelectric-based nanopores.

Recently, there has been growing interest in applying nanopores as sensors for rapid analysis of biomolecules (DNA, RNA, protein, etc). Special emphasis has been given to applications of nanopores for DNA sequencing, as this technology holds the promise to reduce the cost of sequencing below $1000/human genome. An issue in these applications is the control of the translocation of DNA through the nanopore.

Nanopore sequencing is a method for determining the order in which nucleotides occur on a strand of DNA. A nanopore is simply a small hole of the order of 1 nanometer in internal diameter. The theory behind nanopore sequencing has to do with what occurs when the nanopore is immersed in a conducting fluid and a potential (voltage) is applied across it: under these conditions a slight electric current due to conduction of ions through the nanopore can be observed, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be put around the nanopore so that DNA bases can be differentiated while the DNA passes through the nanopore.

DNA could be passed through the nanopore for various reasons. For example, electrophoresis might attract the DNA towards the nanopore, and it might eventually pass through it. Also, enzymes attached to the nanopore might guide DNA towards the nanopore. The scale of the nanopore means that the DNA may be forced through the hole as a long string, one base at a time, rather like thread through the eye of a needle. As it does so, each nucleotide on the DNA molecule may obstruct the nanopore to a different, characteristic degree. The amount of current which can pass through the nanopore at any given moment therefore varies depending on whether the nanopore is blocked by an A, a C, a G or a T. The change in the current through the nanopore as the DNA molecule passes through the nanopore represents a direct reading of the DNA sequence. Alternatively, other electrical or optical sensors can also be put around the nanopore to identify individual DNA bases as they pass through the nanopore in the correct order. The potential of this nanopore DNA sequencing approach is that a single molecule of DNA can be sequenced directly using a nanopore, without the need for an intervening PCR amplification step or a chemical labeling step or the need for optical instrumentation to identify the chemical label.

BRIEF SUMMARY

According to one exemplary embodiment, a method is provided for fabricating an apparatus by applying piezoelectric material for controlling a polymer through a nanopore. A reservoir is formed filled with conductive fluid. A membrane is formed that separates the reservoir. A nanopore is formed through the membrane. The membrane comprises electrical conductive layers, piezoelectric layers, and insulating layers. The piezoelectric layers are operative to control a size of the nanopore and the relative distance between the upper and underneath layers when a voltage is applied to the piezoelectric layers.

Other systems, methods, apparatus, design structures, and/or computer program products according to embodiments will be or become apparent to one with skill in the art upon review of the following drawings and detailed description. It is intended that all such additional systems, methods, apparatus, design structures, and/or computer program products be included within this description, be within the scope of the exemplary embodiments, and be protected by the accompanying claims. For a better understanding of the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features are apparent from the following detailed description taken in conjunction with the accompanying drawings in which:

FIG. 4 illustrates a schematic of a nanopore made of piezoelectric material in accordance with exemplary embodiments.

FIG. 7 shows a block diagram of an exemplary design flow used for example, in semiconductor IC logic design, simulation, test, layout, and manufacture according to exemplary embodiments.

DETAILED DESCRIPTION

One of the main challenges to nanopore DNA sequencing approach is to control the motion of DNA through the nanopore, precisely and slowing enough for allowing detecting each single base. The present disclosure provides techniques and mechanisms to use piezoelectric material to clamp and move DNA or any other polymers through the nanopore at any electrically controlled speed. For example, exemplary embodiments provide a method to address issues of controlling the motion of DNA or any other polymers through the nanopore using embedded piezoelectric layers in the nanopore and/or in the membrane that the nanopore is made through.

Exemplary embodiments are based on a nanopore drilled through piezoelectric material and other materials. Exemplary embodiments provide a micro-electromechanical device designed to control the motion of polymers, such as DNA, RNA, etc., through the nanopore.

In the present disclosure, exemplary embodiments utilize piezoelectric materials as part of the walls surrounding the nanopore and/or as part of the membrane that the nanopore is made through, in such a way that the size of the nanopore can be electrically tuned to clamp and release polymers, such as DNA molecules, passing through the nanopore.

Combined with the electrical driving force on DNA and/or with another set of parts made of piezoelectric material, exemplary embodiments can control the motion of DNA with nanometer (nm) resolution. By utilizing parts made of piezoelectric material, all the clamping, releasing, and driving of the polymers can be solely dependent on the static frictional force between the polymer and the wall of the nanopore, and this process can be generally applied to any polymers (charged or uncharged).

Figure 1A:
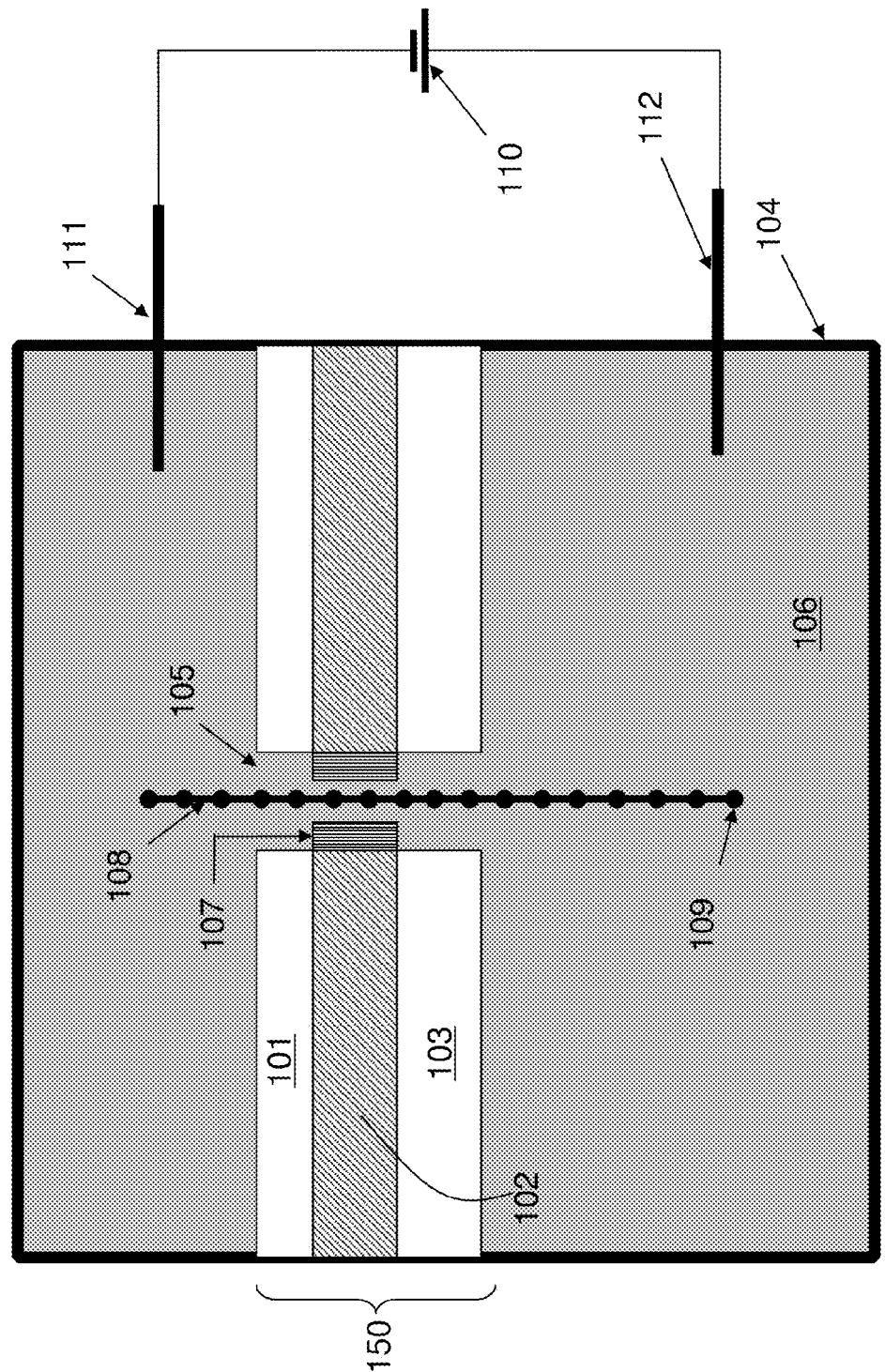
FIGS. 1A and 1B illustrate a schematic of a nanopore made of piezoelectric material, combining with electrical diving force, to control the motion of polymers through the nanopore in accordance with exemplary embodiments.
Figure 1B:
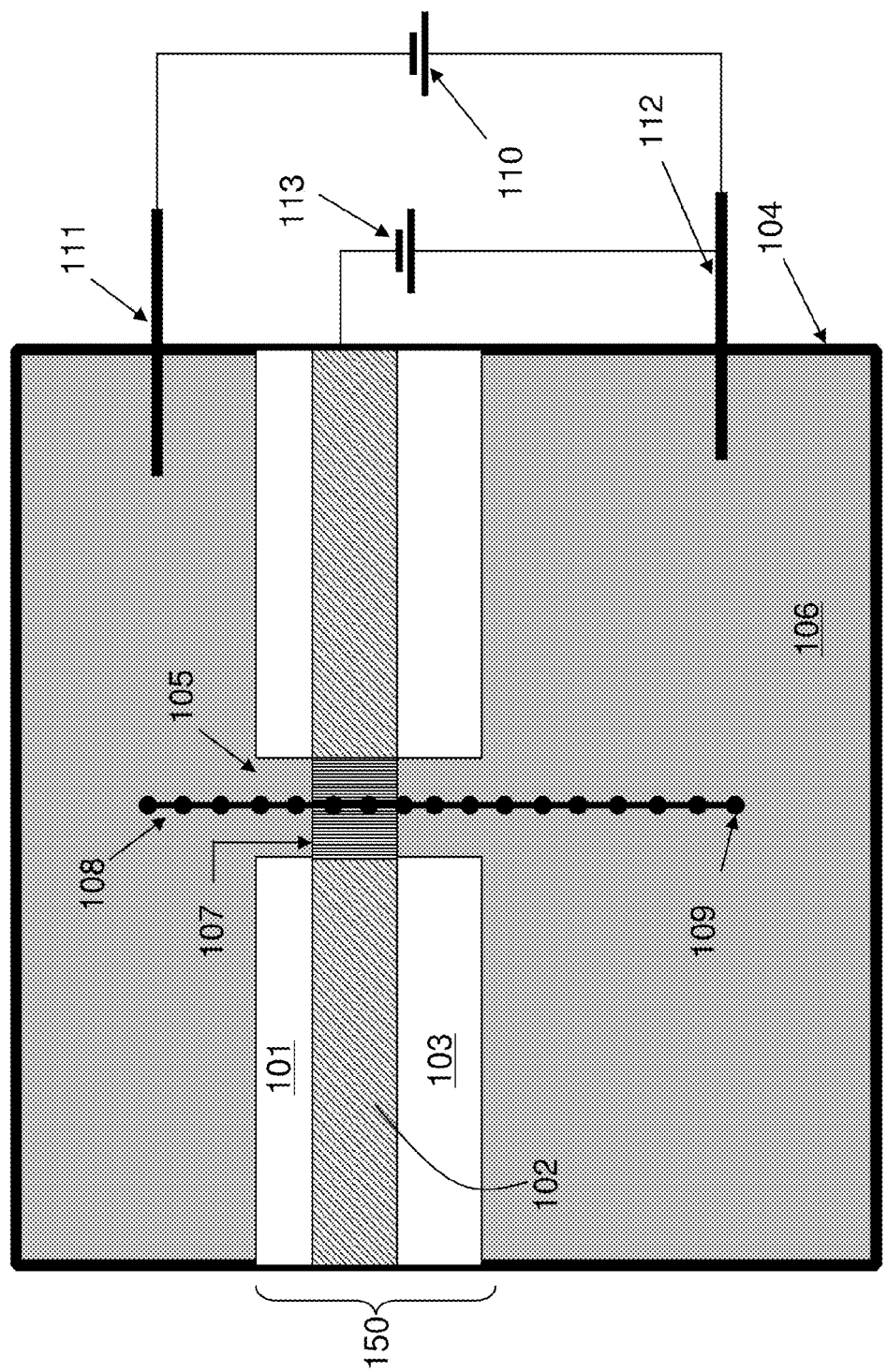

With reference now to FIGS. 1A and 1B, FIGS. 1A and 1B illustrate a cross-section schematic of a nanopore made of piezoelectric materials, combined with an electrical diving force, to prompt the motion of a polymer, such as DNA, through the nanopore in accordance with exemplary embodiments.

A membrane 150 comprising films 101, 102, and 103 partitions reservoir 104 into two parts. A nanometer size hole 105, referred to as a nanopore, is made through the membrane 150. The reservoir 104 and the hole 105 are then filled with ionic buffer (fluid) 106. The film 102 of the membrane 150 needs to be electrically conductive while the films 101 and 103 need to be electrically insulating, to isolate film 102 from the conductive ionic buffer 106. The reservoir 104 is an insulated container that is configured to hold the solution of the conductive ionic buffer 106.

Piezoelectric material of a circular shape 107 is in the inner surface of the hole 105 and is sandwiched between the electrically conductive film 102 and the ionic buffer 106. Charged polymers 108 (charges are illustrated as 109) are loaded into the hole 105 by an electrical voltage bias 110 that is applied across the hole 105 via two electrochemical electrodes 111 and 112, which were dipped in the ionic buffers 106 of the two parts of reservoir 104.

Now turning to FIG. 1B, FIG. 1B illustrates another voltage bias 113 that is applied between the electrically conductive film 102 and the ionic buffer 106. The voltage bias 113 can tune the size of the hole 105 in the piezoelectric material 107 to control the clamping and/or releasing of the charged polymer 108. As seen in FIG. 1B, the piezoelectric circular shaped material 107 is clamped to hold the polymer 108. If either of the voltage biases 110 and/or 113 is pulsed, the charged polymer 108 can then be driven through the hole 105 in a controlled fashion.

With reference to FIGS. 2A, 2B, 2C, 2D, 2E, 2F, 2G, and 2F, FIGS. 2A, 2B, 2C, 2D, 2E, 2F, 2G, and 2F illustrate a cross-section schematic of a nanopore made of several piezoelectric parts (films), to control the motion of DNA (or any polymer) through the nanopore in accordance with exemplary embodiments. Since the nanodevice in FIGS. 2A-F does not rely on electrical forces on the polymer 211 to drive the polymer (as in FIGS. 1A and 1B), the nanodevice can be applied for any polymer including the uncharged polymer 211 (or a charged polymer).

Figure 2A:
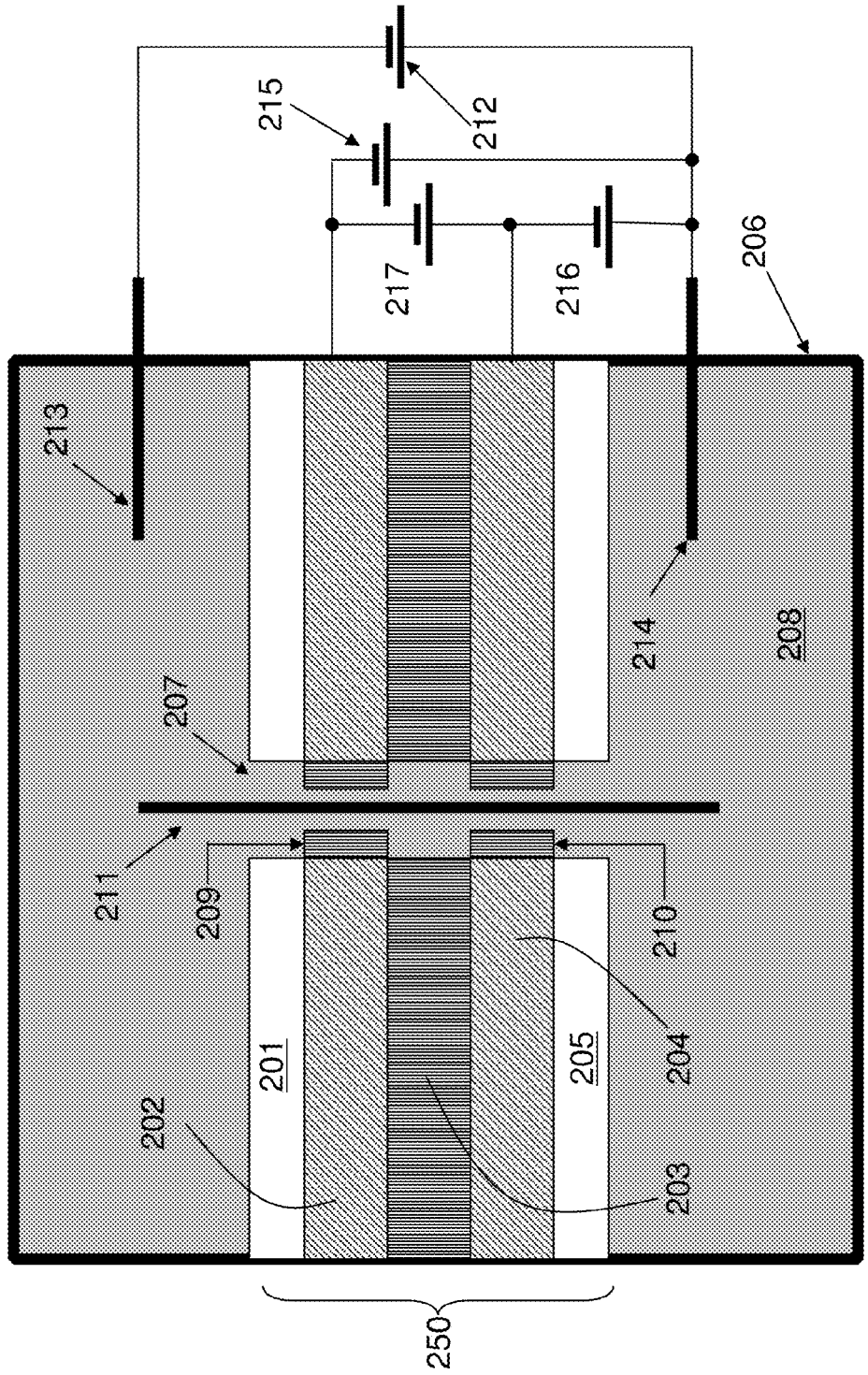
FIGS. 2A, 2B, 2C, 2D, 2E, 2F, 2G, and 2H illustrate a schematic of a nanopore made of several piezoelectric parts, to control the motion of polymers through the nanopore in accordance with exemplary embodiments.

Now turning to FIG. 2A, a membrane 250, which comprises films 201, 202, 203, 204 and 205, partitions reservoir 206 into two parts. A nanometer size hole 207 is made through the membrane 250. The reservoir 206 and the hole 207 are then filled with ionic buffer (fluid) 208. Membrane films 202 and 204 are electrically conductive while membrane films 201 and 205 are electrically insulating to isolate films 202 and 204 from the conductive ionic buffer 208. Membrane film 203 is made of piezoelectric material. Piezoelectric material of circular shape 209 and 210 are in the inner surface of the hole 207. The circular shaped piezoelectric material 209 is sandwiched between the electrically conductive film 202 and the ionic buffer 208. The circular shaped piezoelectric material 210 is sandwiched between the electrically conductive film 204 and the ionic buffer 208.

Figure 2B:
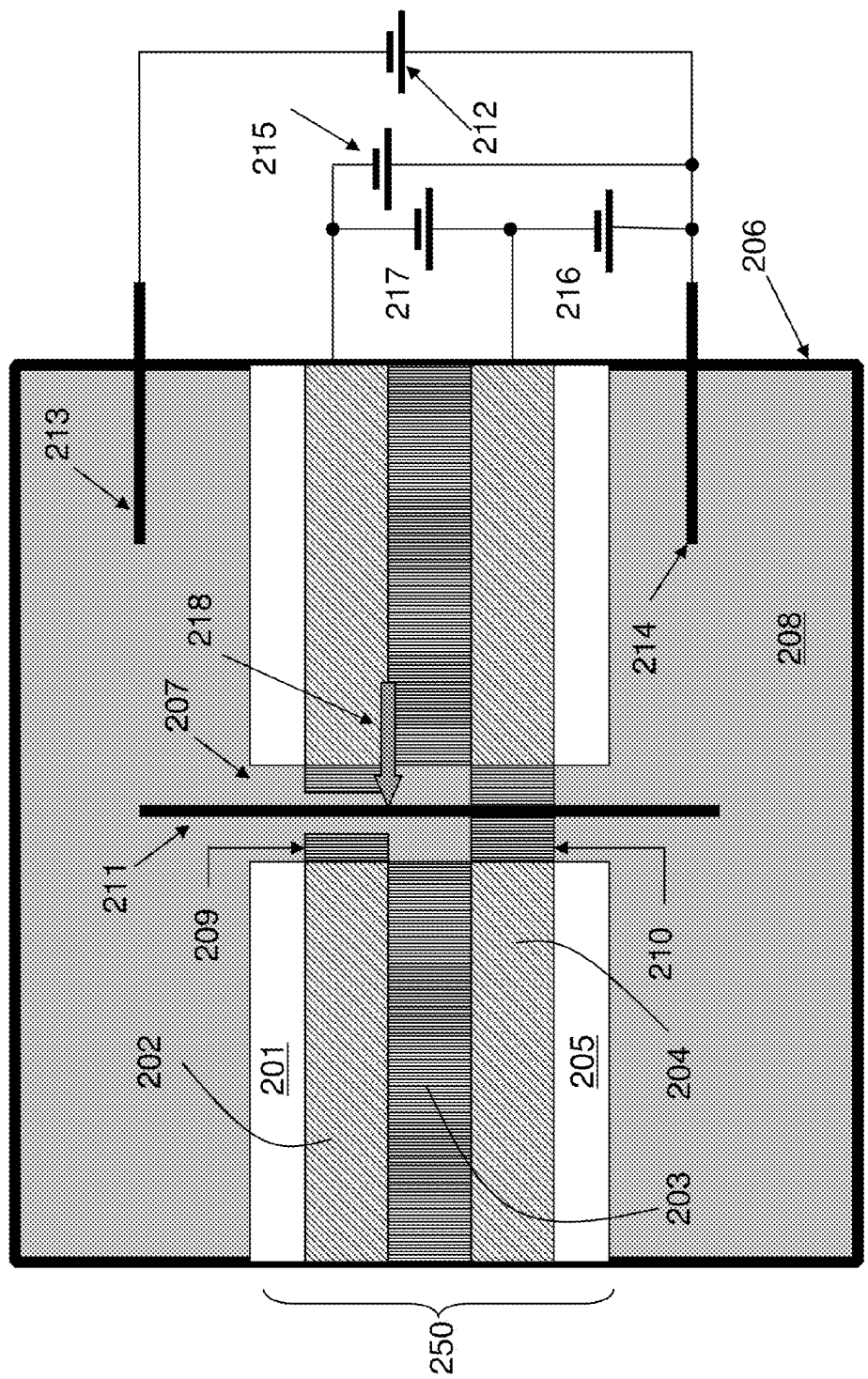

Polymer 211 can be loaded into the hole 207 by an electrical voltage bias 212 (if the polymer 211 is charged) applied across the hole 207 via two electrochemical electrodes 213 and 214, which were dipped in the ionic buffer 208 of the two parts of reservoir 206. If the polymer 211 is not charged, the polymer 211 can also be loaded into hole 207 by pressure bias between the two parts of reservoir, as shown in FIG. 2H. In FIG. 2H, one inlet is made at the upper part of reservoir 206 and one outlet is made at the lower part of reservoir 206. Two plungers 218 and 219 are employed to seal the inlet and outlet respectively. Forces applied on plungers 218 and 219 will force ionic buffer 208, together with polymers 211 that are in the buffer 208, to flow from the upper part of the reservoir 206 to the lower part of the reservoir 206 through the nanopore 207. Since the presence of polymer 211 in the nanopore 207 can be detected from the change of ionic current between electrodes 213 and 214, the forces applied on plungers 218 and 219 can be stopped as soon as the polymer 211 enters the nanopore 207. This completes the loading process of an uncharged polymer 211 into the nanopore 207.

Referring back to FIG. 2A, a voltage bias 215 is applied between the electrically conductive film 202 and the ionic buffer 208, which can tune the size of the hole 207 between the piezoelectric material 209, thus controlling the clamping and releasing of the charged (or uncharged) polymer 211 at that location of film 202. Voltage bias 216 is applied between the electrically conductive film 204 and the ionic buffer 208, which can tune the size of the hole 207 at the piezoelectric material 210, thus controlling the clamping and releasing of the charged (or uncharged) polymer 207 at that location of film 204.

Voltage bias 217 is applied between the two electrically conductive films 202 and 204, which can tune the thickness of film 203. As shown in FIG. 2B, by changing voltage 216, the piezoelectric clamp 210 can clamp the polymer 211 at the location of the film 204. Arrow 218 indicates the relative position of the polymer 211 to film 202.

Figure 2C:
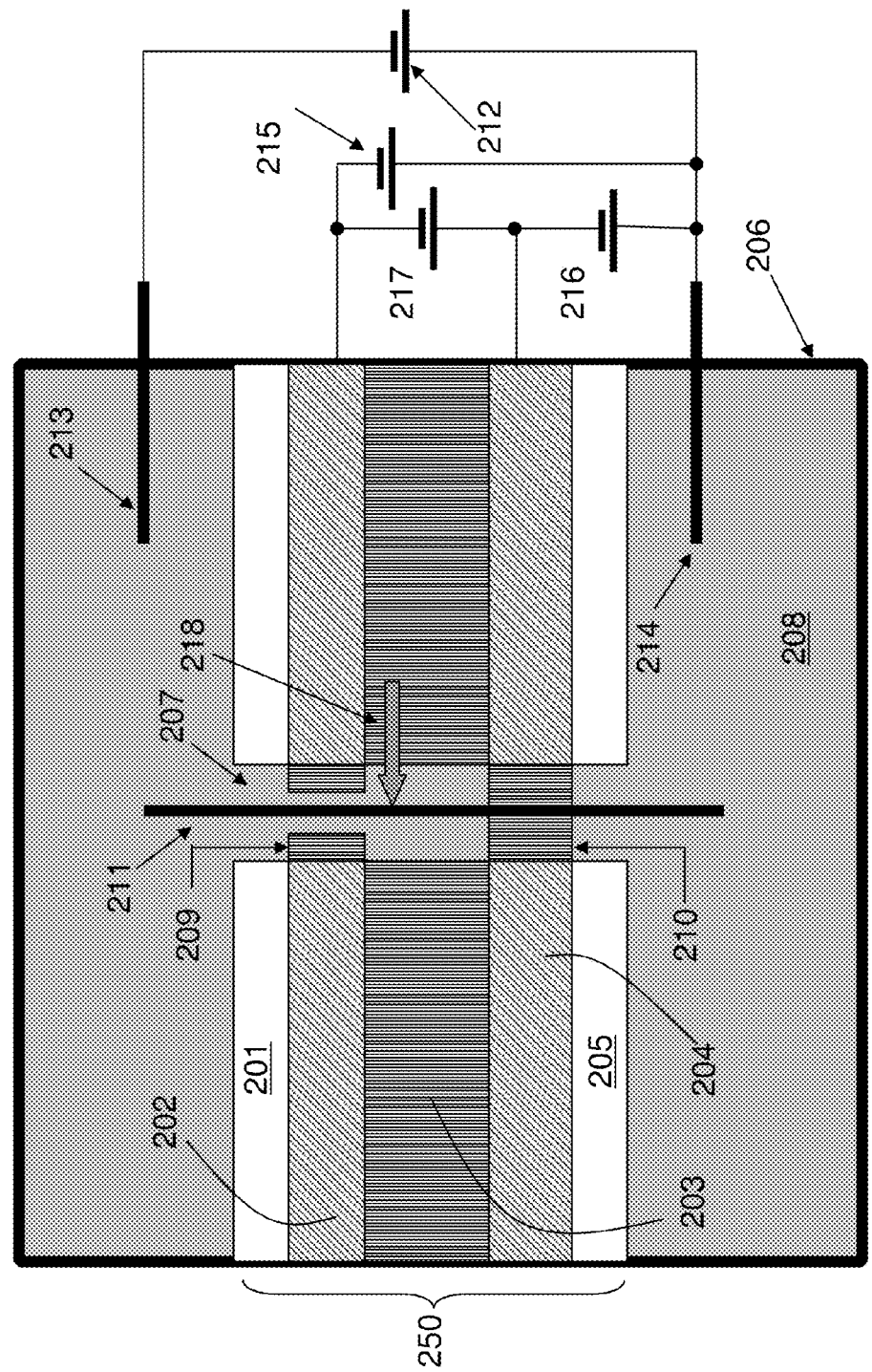
Figure 2D:
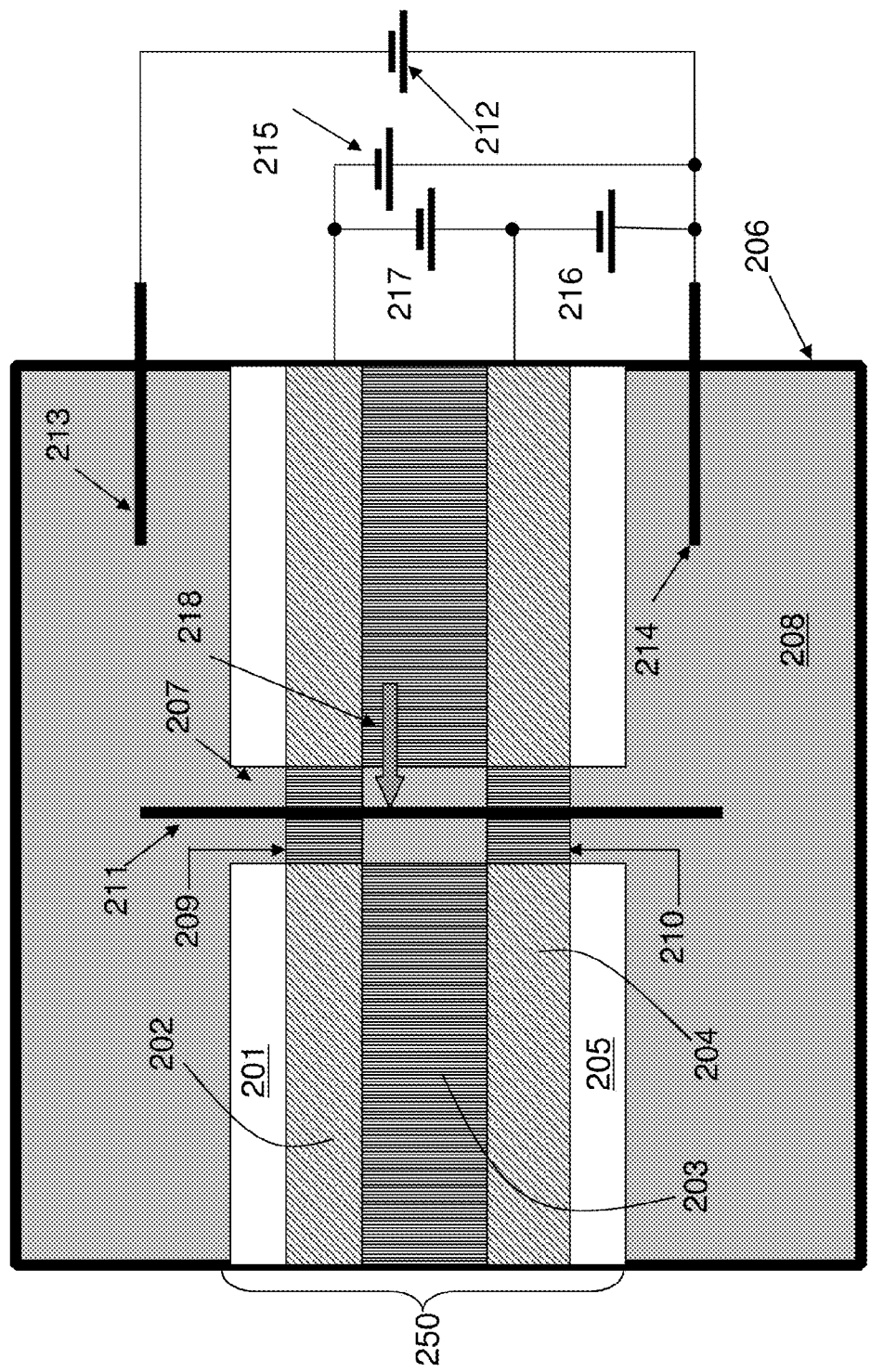
Figure 2E:
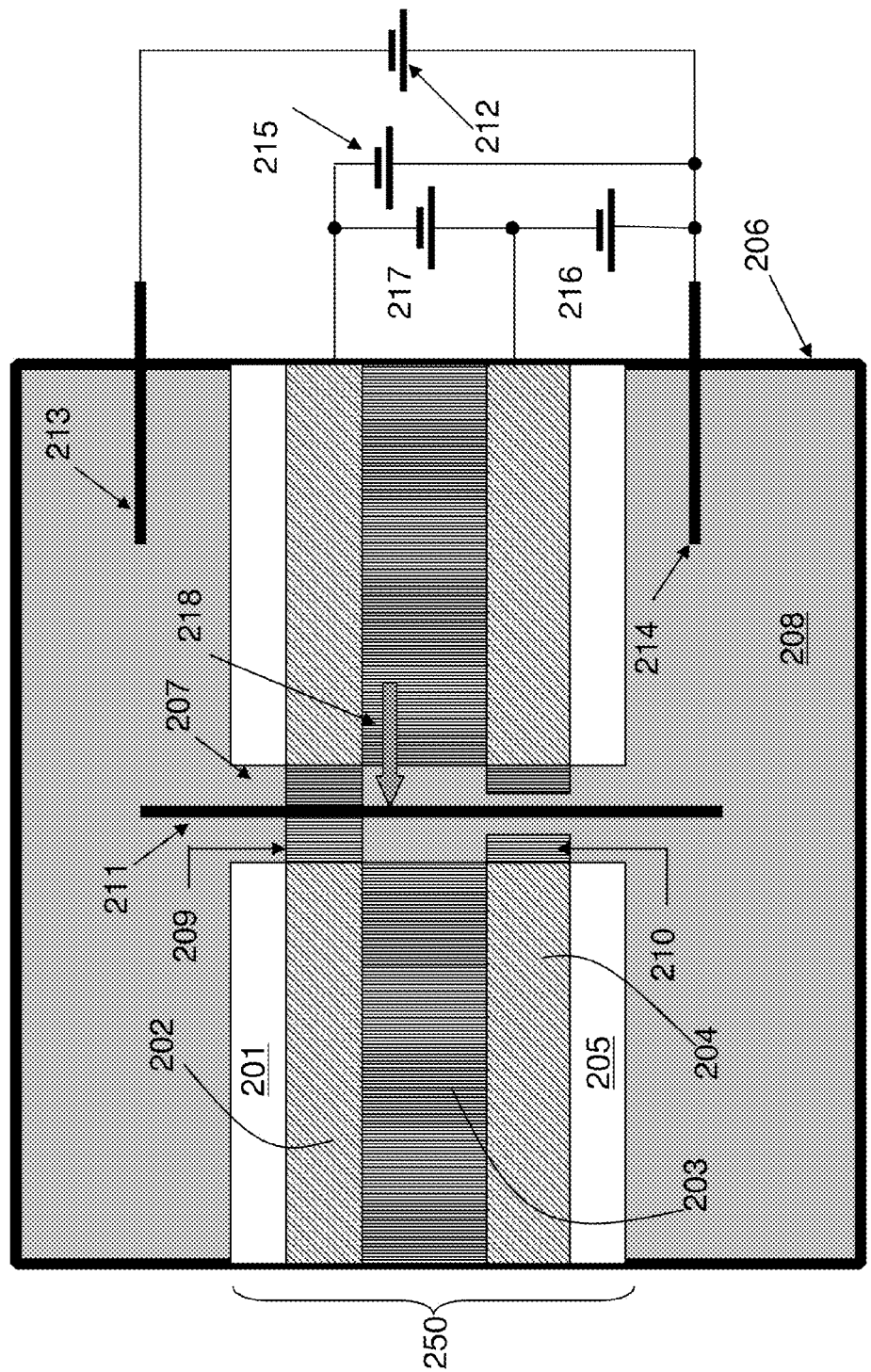
Figure 2F:
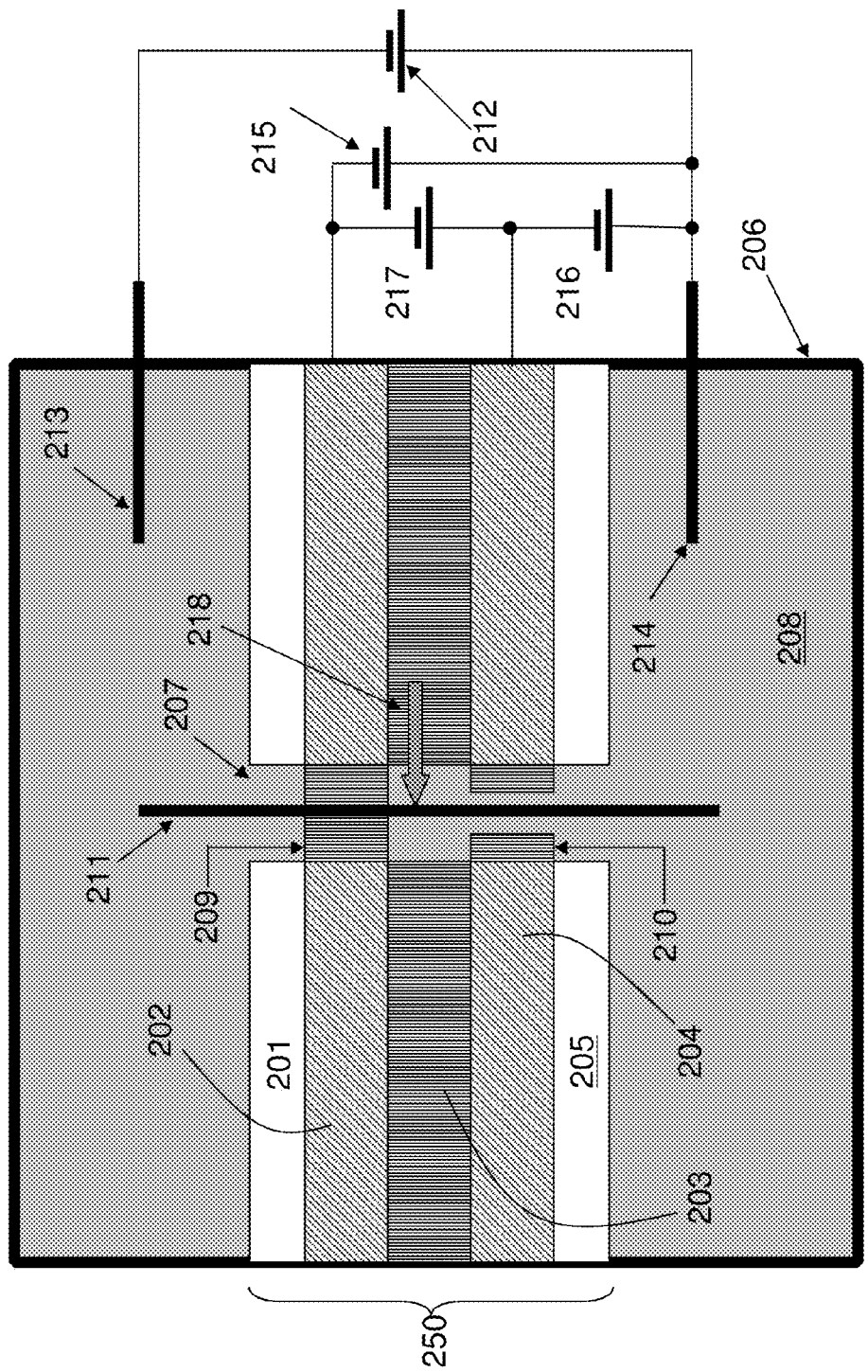
Figure 2G:
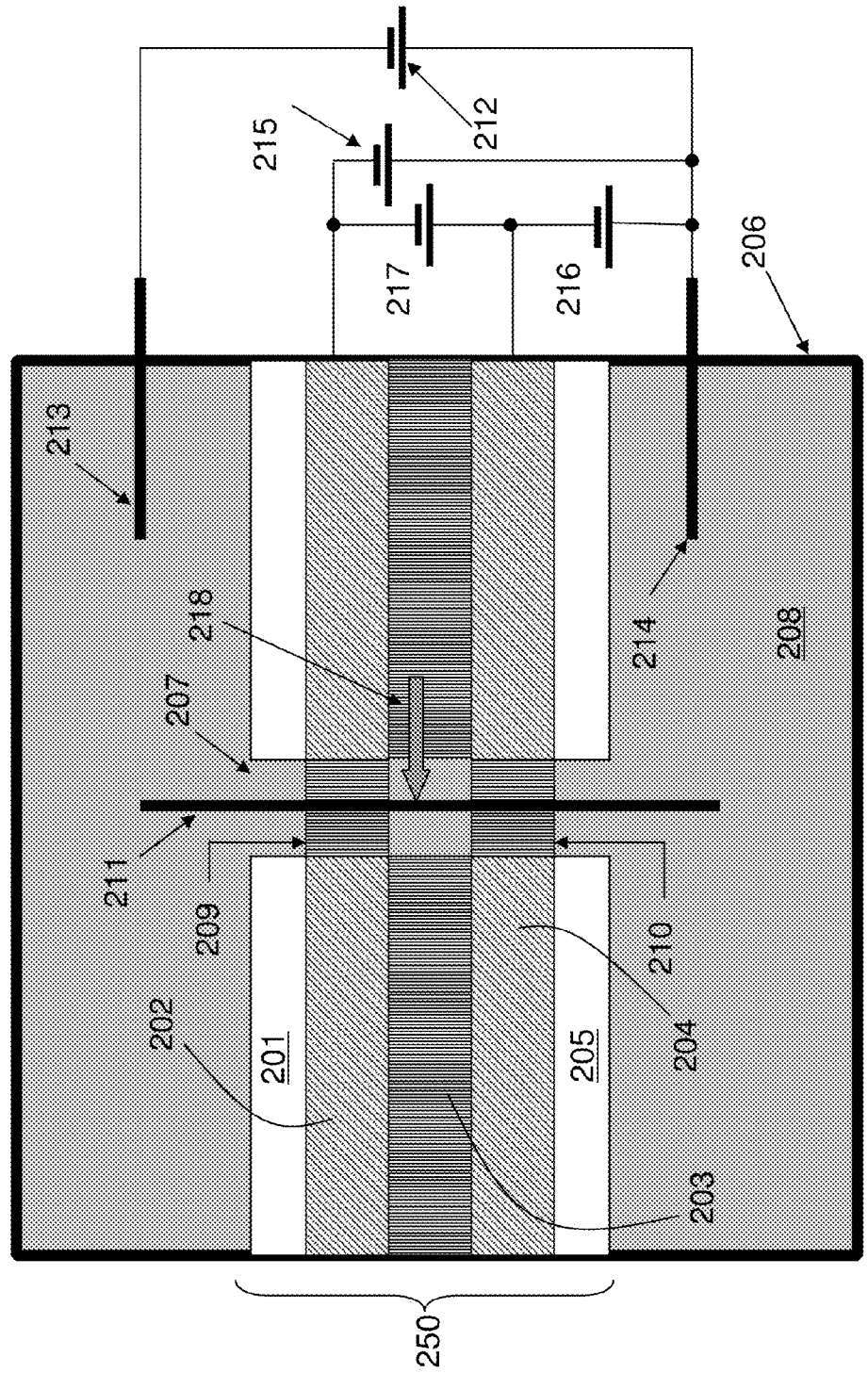
Figure 2H:
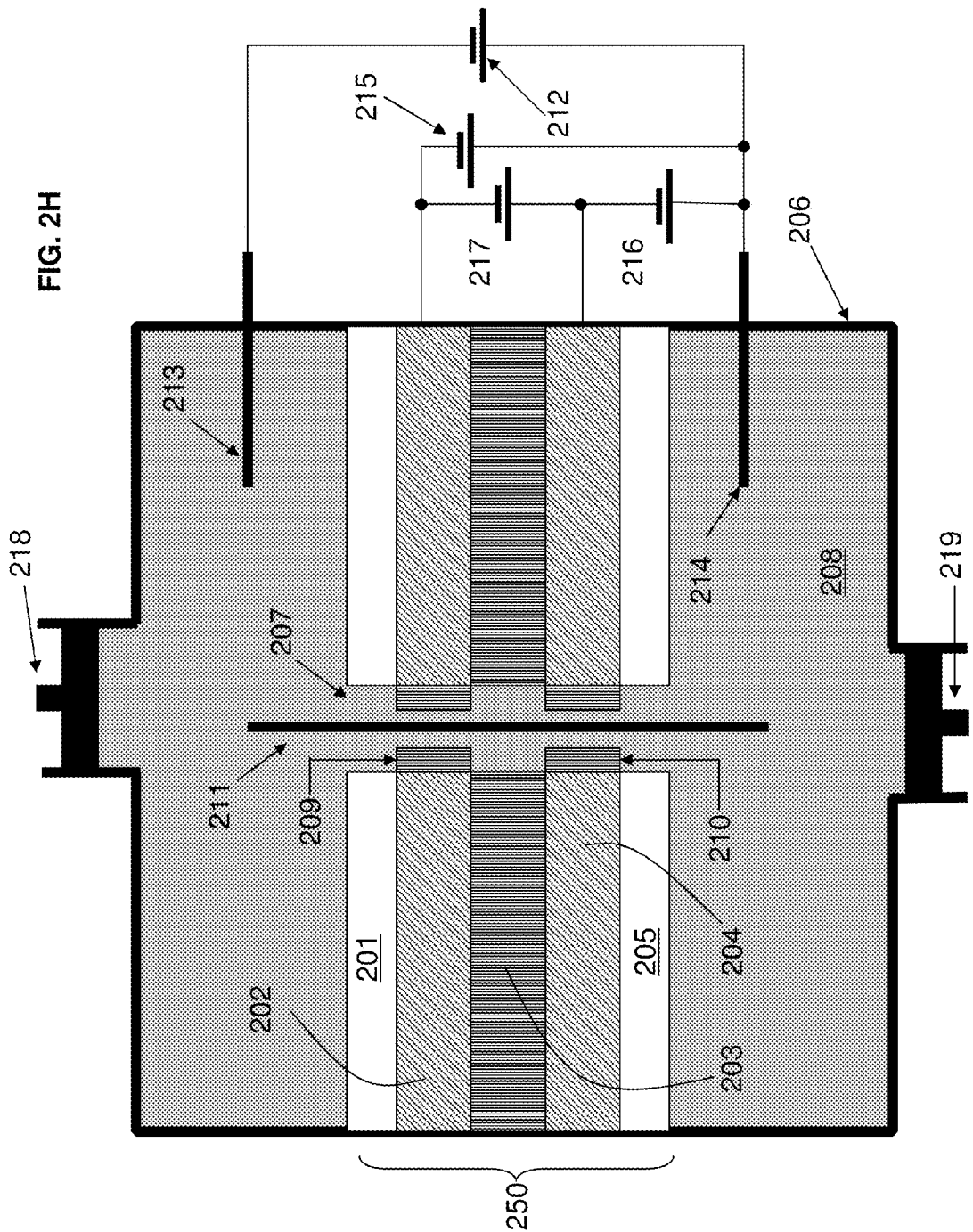

As shown in FIG. 2C, one can then tune the voltage 217 to increase (or decrease) the thickness of the film 203 and change the relative position (shown by the arrow 218) of the film 202 to the clamped polymer 211. Accordingly the film 202 is shifted upwards (or downwards) relative to the arrow 218 due to the increasing (or decreasing) of the thickness of the piezoelectric film 203. As shown in FIG. 2D, by changing voltage 215, the polymer 211 is clamped by the piezoelectric clamp 209 at the position of the film 202. As shown in FIG. 2E, by changing voltage 216, the piezoelectric clamp 210 at position of film 204 is released. As shown in FIG. 2F, by changing voltage 217, film 203 is recovered to its original thickness as in FIG. 2B. As shown in FIG. 2G, by changing voltage 216, one can clamp the polymer 207 with the piezoelectric clamp 210 at the location of the film 204. Then, by changing voltage 215, the piezoelectric clamp 209 at position of film 202 is released, and the device is recovered to its original state as shown in FIG. 2B while the polymer 211 is moved downwards (or upwards).

FIGS. 2B through 2G show one cycle for moving the polymer 211 downward. One can then start other cycles to move the polymer 211 a small step per cycle. That is, the piezoelectric clamps 209 and 210 can be clamped and released in conjunction with elongating and shorting the piezoelectric material 203 to drive the polymer 211 through the hole 207. Further, in exemplary embodiments, one can use the two clamping points (at piezoelectric clamp 209 and piezoelectric clamp 210) to stretch the polymer 211 and break the polymer 211 at a specific location (which is any specific location chosen by the user) as discussed below in FIGS. 3A, 3B, and 3C.

Figure 3A:
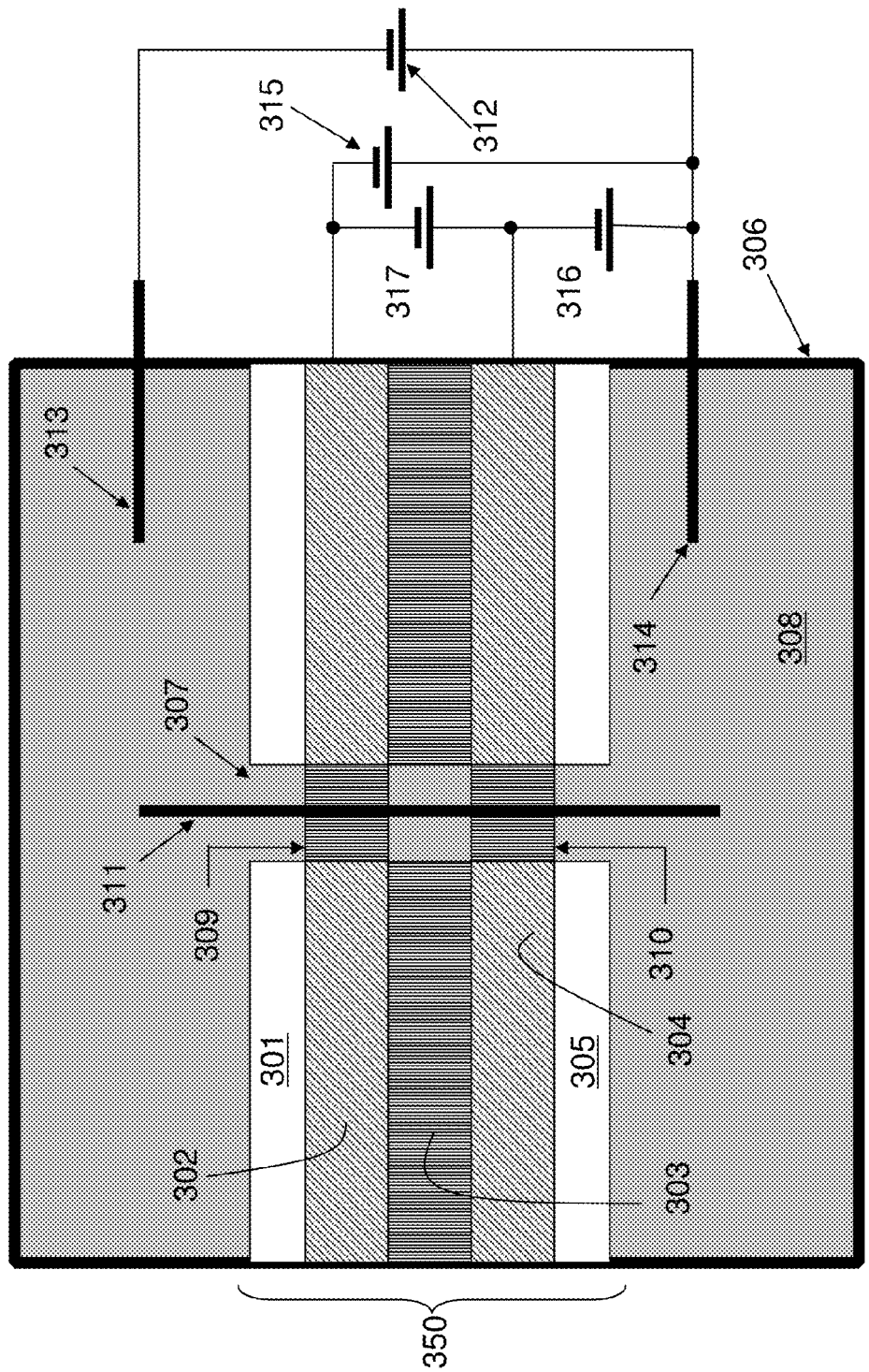
FIGS. 3A, 3B, and 3C illustrate a schematic of a nanopore made of several piezoelectric parts to stretch and break a polymer in accordance with exemplary embodiments.
Figure 3B:
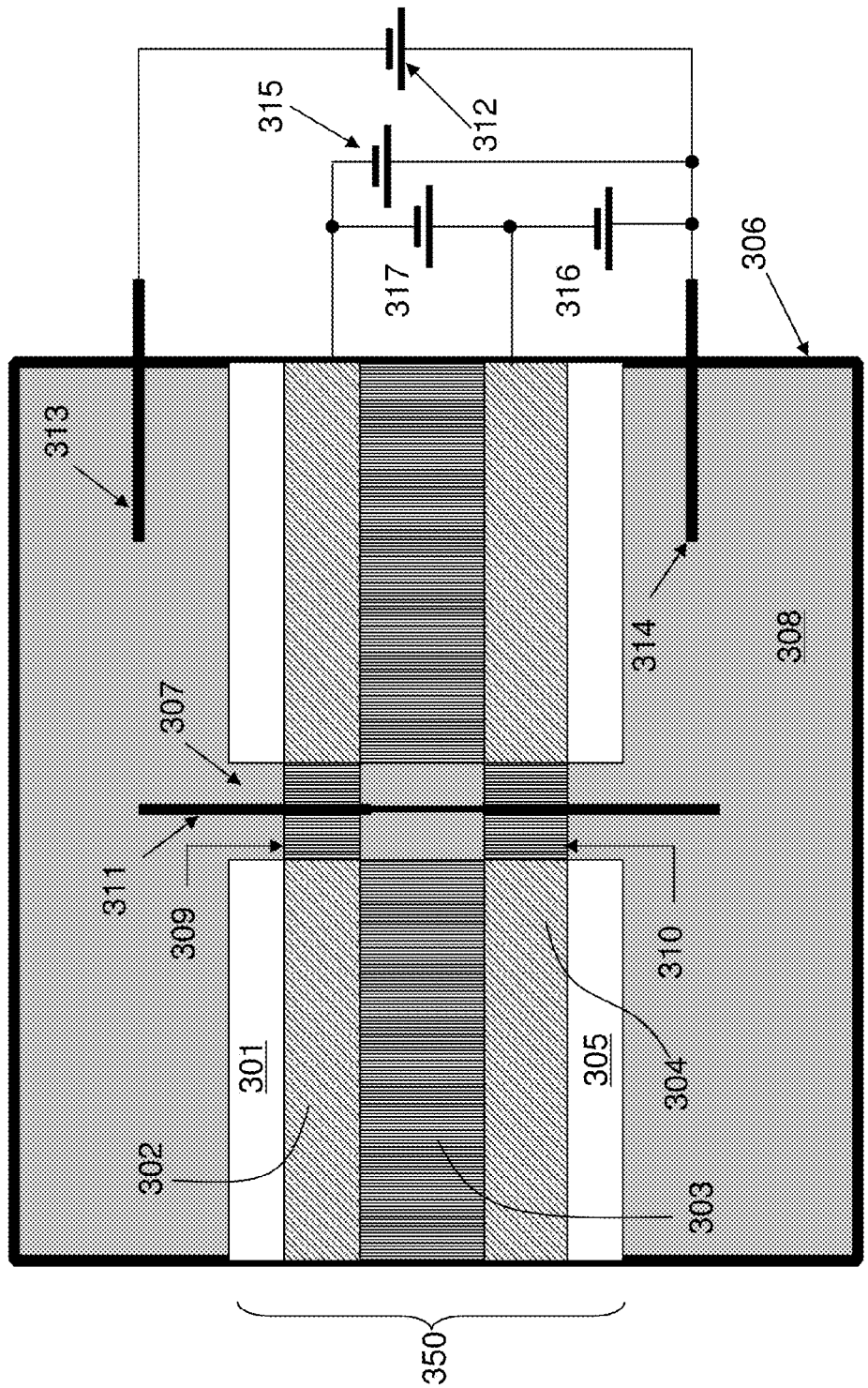
Figure 3C:
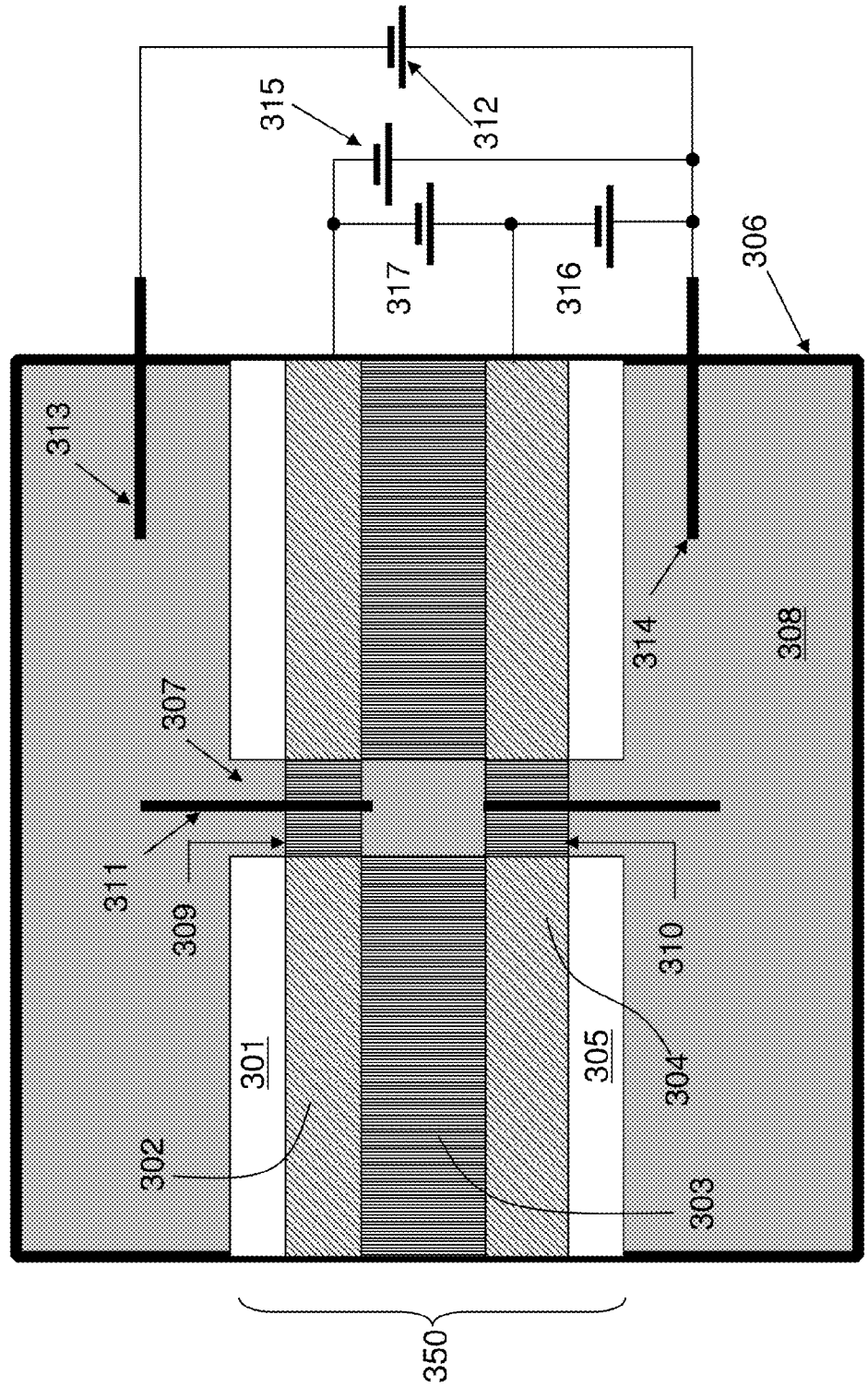

FIGS. 3A, 3B, and 3C illustrate a cross-section schematic of a nanopore made of several piezoelectric parts (films), to stretch and break a polymer in the nanopore at specific location in accordance with exemplary embodiments. As shown in FIGS. 3A, 3B, and 3C, parts 301-317 correspond to part 201-217 in FIGS. 2A-2G, respectively.

By changing voltages 316 and 317, one can clamp the polymer 311 at locations of films 302 and 304 with piezoelectric clamps 309 and 310. As shown in FIG. 3B, by tuning the voltage 317 to increase the thickness of the film 303, one can stretch the clamped polymer 311 and break it. FIG. 3C shows the broken polymer 311. If desired, the user may not break the polymer 311 but only stretch the polymer 311 to a desired length.

The piezoelectric material of circular shapes 107 in FIG. 1 and piezoelectric material of circular shapes 209 and 210 in FIG. 2 may be difficult to fabricate, because the circular shapes 107, 209, and 210 are fabricated in the nanopore after the hole is drilled. As an alternative, the circular shaped piezoelectric material 107, 209, and 210 do not have to be deposited after the hole is drilled.

FIG. 4 illustrates a cross-section of a schematic of a nanopore made of several piezoelectric parts (films), to control the motion of DNA (or any polymer) through the nanopore in accordance with exemplary embodiments. As shown in FIG. 4, parts 401-413 correspond to parts 101-113 in FIGS. 1A and 1B and are configured to work as discussed above in FIGS. 1A and 1B. The piezoelectric material of circular shapes 407 in FIG. 4 are deposited and patterned before the hole 405 in FIG. 4 is drilled. The piezoelectric material 407 is configured to clamp the charged polymer 408 as explained in FIGS. 1A and 1B. In FIG. 4, the piezoelectric clamp 407 is operative to clamp the polymer 408 and control the polymer 408 just as the piezoelectric clamp 107.

Figure 5:
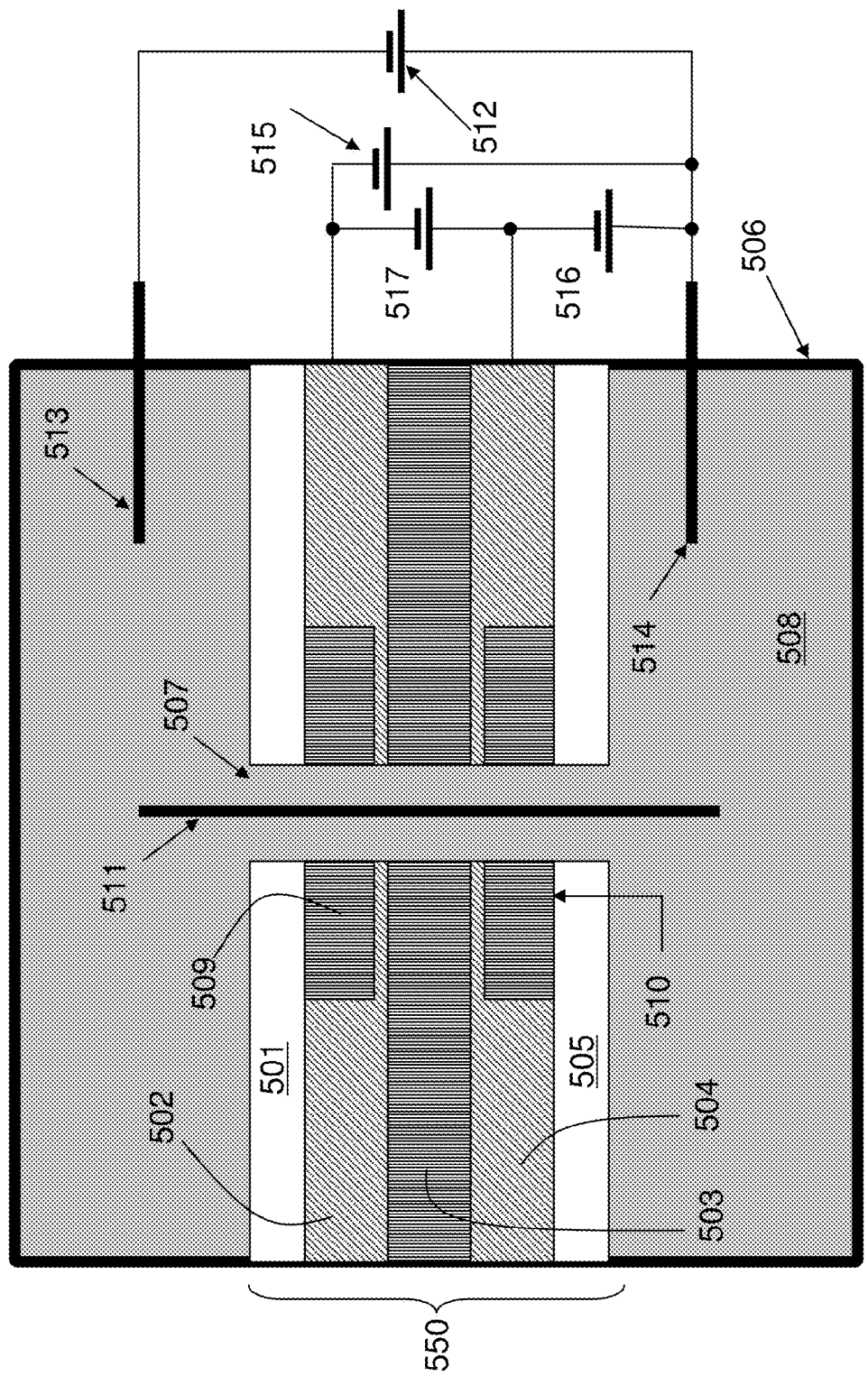
FIG. 5 illustrates a schematic of a nanopore made of several piezoelectric parts in accordance with exemplary embodiments.

FIG. 5 illustrates a cross-section of a schematic of a nanopore made of several piezoelectric parts (films), to control the motion of DNA (or any polymer) through the nanopore in accordance with exemplary embodiments. As shown in FIG. 5, parts 501-517 correspond to parts 201-217 in FIGS. 2A-2G and are configured to work as discussed above in FIGS. 2A-2G to control the motion of DNA (or any polymer) through the nanopore in accordance with exemplary embodiments. The piezoelectric material of circular shapes 509 and 510 in FIG. 5 are deposited and patterned before the hole 507 in FIG. 5 is drilled. Also, as illustrated in FIGS. 3A-3C, the nanodevice in FIG. 5 is configured to stretch and break the polymer 511 as discussed above in FIGS. 3A-3C. In FIG. 5, the piezoelectric clamps 509 and 510 are operative to clamp the polymer 511 in two places to stretch and break the polymer 511 by expanding the piezoelectric material 503, just as the piezoelectric clamps 309 and 310 and the piezoelectric material 303 in FIGS. 3A-3C.

Figure 6:
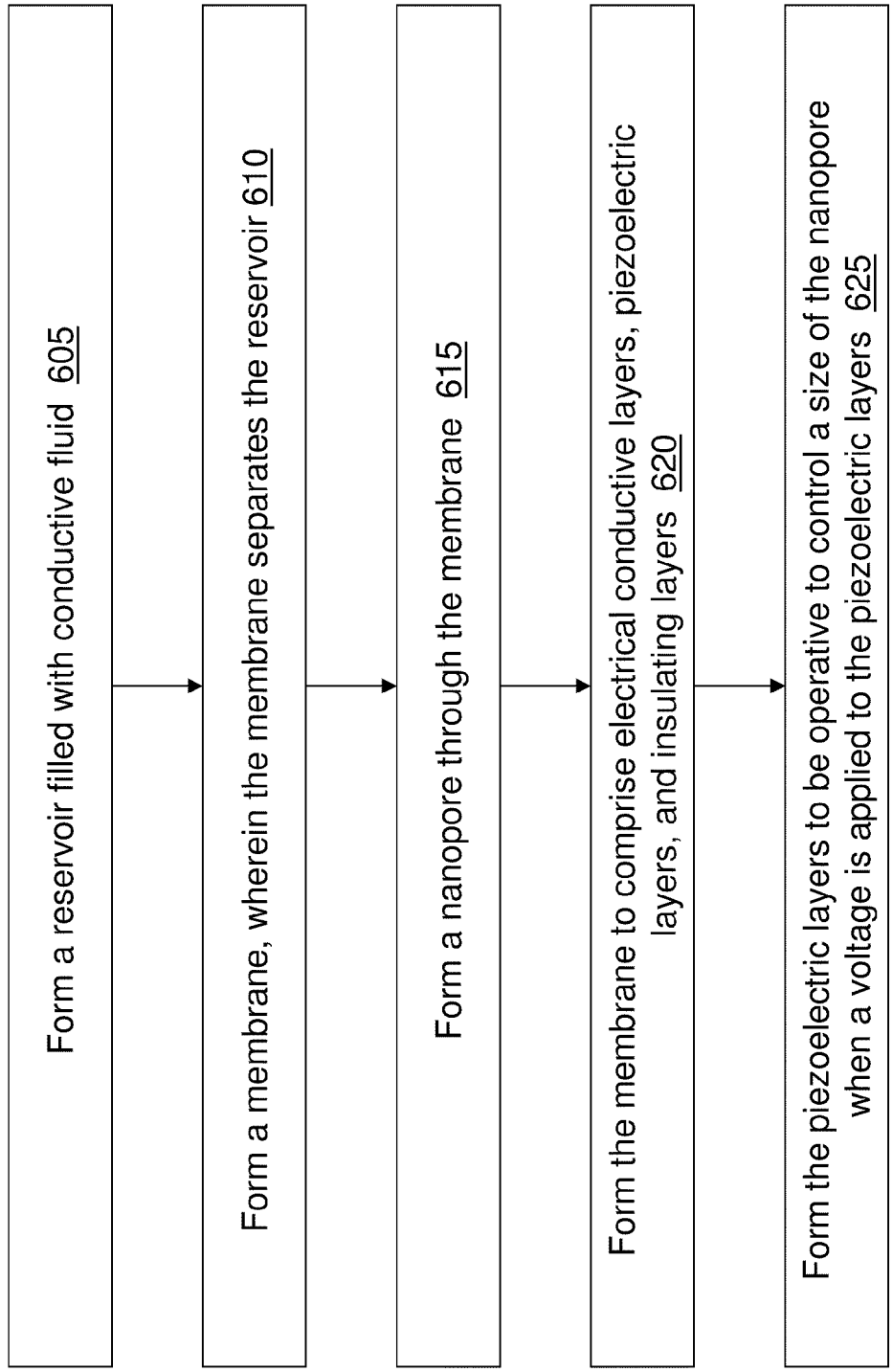
FIG. 6 illustrates a method in accordance with exemplary embodiments.

FIG. 6 illustrates a method for fabricating an apparatus by applying piezoelectric material for controlling a polymer through a nanopore in accordance with exemplary embodiments, e.g., as in FIGS. 1A, 1B, 2A-2G, 3A-3C, 4, and 5. A reservoir is filled with conductive fluid at 605.

A membrane is formed and the membrane separates the reservoir at 610.

A nanopore is formed through the membrane at 615.

The membrane is formed to comprise electrical conductive layers, piezoelectric layers, and insulating layers at 620.

The piezoelectric layers are formed to be operative to control a size of the nanopore when a voltage is applied to the piezoelectric layers at 625.

Further, the piezoelectric layers are formed to be operative to control the thickness of part of the membrane when a voltage is applied to the piezoelectric layers. The piezoelectric layers are formed to be operative to drive a piezoelectric-layer-clamped polymer through the nanopore when a voltage is applied to the piezoelectric layers.

Also, the piezoelectric layers are formed to be operative to clamp a polymer in the nanopore when a voltage is applied to the piezoelectric layers. The piezoelectric layers are operative to be formed to stretch a polymer in the nanopore when a voltage is applied to the piezoelectric layers.

Additionally, the piezoelectric layers are formed to be operative to break a polymer in the nanopore when a voltage is applied to the piezoelectric layers. The piezoelectric layers are formed to be operative to clamp a polymer at two locations to break the polymer when a voltage is applied to the piezoelectric layers. The piezoelectric layers are formed to be operative to increase (or decrease) in thickness to move a piezoelectric-layer-clamped polymer through the nanopore when a voltage is applied to the piezoelectric layers.

FIG. 7 shows a block diagram of an exemplary design flow 700 used for example, in semiconductor IC logic design, simulation, test, layout, and manufacture. Design flow 700 includes processes, machines and/or mechanisms for processing design structures or devices to generate logically or otherwise functionally equivalent representations of the design structures and/or devices described above and shown in FIGS. 1A, 1B, 2A-2H, 3A-3C, 4, and 5. The design structures processed and/or generated by design flow 700 may be encoded on machine-readable transmission or storage media to include data and/or instructions that when executed or otherwise processed on a data processing system generate a logically, structurally, mechanically, or otherwise functionally equivalent representation of hardware components, circuits, devices, or systems. Machines include, but are not limited to, any machine used in an IC design process, such as designing, manufacturing, or simulating a circuit, component, device, or system. For example, machines may include: lithography machines, machines and/or equipment for generating masks (e.g. e-beam writers), computers or equipment for simulating design structures, any apparatus used in the manufacturing or test process, or any machines for programming functionally equivalent representations of the design structures into any medium (e.g. a machine for programming a programmable gate array).

Design flow 700 may vary depending on the type of representation being designed. For example, a design flow 700 for building an application specific IC (ASIC) may differ from a design flow 700 for designing a standard component or from a design flow 700 for instantiating the design into a programmable array, for example a programmable gate array (PGA) or a field programmable gate array (FPGA) offered by Altera® Inc. or Xilinx® Inc.

FIG. 7 illustrates multiple such design structures including an input design structure 720 that is preferably processed by a design process 710. Design structure 720 may be a logical simulation design structure generated and processed by design process 710 to produce a logically equivalent functional representation of a hardware device. Design structure 720 may also or alternatively comprise data and/or program instructions that when processed by design process 710, generate a functional representation of the physical structure of a hardware device. Whether representing functional and/or structural design features, design structure 720 may be generated using electronic computer-aided design (ECAD) such as implemented by a core developer/designer. When encoded on a machine-readable data transmission, gate array, or storage medium, design structure 720 may be accessed and processed by one or more hardware and/or software modules within design process 710 to simulate or otherwise functionally represent an electronic component, circuit, electronic or logic module, apparatus, device, or system such as those shown in FIGS. 1A, 1B, 2A-2H, 3A-3C, 4, and 5. As such, design structure 720 may comprise files or other data structures including human and/or machine-readable source code, compiled structures, and computer-executable code structures that when processed by a design or simulation data processing system, functionally simulate or otherwise represent circuits or other levels of hardware logic design. Such data structures may include hardware-description language (HDL) design entities or other data structures conforming to and/or compatible with lower-level HDL design languages such as Verilog and VHDL, and/or higher level design languages such as C or C++.

Design process 710 preferably employs and incorporates hardware and/or software modules for synthesizing, translating, or otherwise processing a design/simulation functional equivalent of the components, circuits, devices, or logic structures shown in FIGS. 1A, 1B, 2A-2H, 3A-3C, 4, and 5 to generate a netlist 780 which may contain design structures such as design structure 720. Netlist 780 may comprise, for example, compiled or otherwise processed data structures representing a list of wires, discrete components, logic gates, control circuits, I/O devices, models, etc. that describes the connections to other elements and circuits in an integrated circuit design. Netlist 780 may be synthesized using an iterative process in which netlist 780 is resynthesized one or more times depending on design specifications and parameters for the device. As with other design structure types described herein, netlist 780 may be recorded on a machine-readable data storage medium or programmed into a programmable gate array. The medium may be a non-volatile storage medium such as a magnetic or optical disk drive, a programmable gate array, a compact flash, or other flash memory. Additionally, or in the alternative, the medium may be a system or cache memory, buffer space, or electrically or optically conductive devices and materials on which data packets may be transmitted and intermediately stored via the Internet, or other networking suitable means.

Design process 710 may include hardware and software modules for processing a variety of input data structure types including netlist 780. Such data structure types may reside, for example, within library elements 730 and include a set of commonly used elements, circuits, and devices, including models, layouts, and symbolic representations, for a given manufacturing technology (e.g., different technology nodes, 32 nm, 45 nm, 90 nm, etc.). The data structure types may further include design specifications 740, characterization data 750, verification data 760, design rules 770, and test data files 785 which may include input test patterns, output test results, and other testing information. Design process 710 may further include, for example, standard mechanical design processes such as stress analysis, thermal analysis, mechanical event simulation, process simulation for operations such as casting, molding, and die press forming, etc. One of ordinary skill in the art of mechanical design can appreciate the extent of possible mechanical design tools and applications used in design process 710 without deviating from the scope and spirit of the invention. Design process 710 may also include modules for performing standard circuit design processes such as timing analysis, verification, design rule checking, place and route operations, etc. Design process 710 employs and incorporates logic and physical design tools such as HDL compilers and simulation model build tools to process design structure 720 together with some or all of the depicted supporting data structures along with any additional mechanical design or data (if applicable), to generate a second design structure 790. Design structure 790 resides on a storage medium or programmable gate array in a data format used for the exchange of data of mechanical devices and structures (e.g. information stored in a IGES, DXF, Parasolid XT, JT, DRG, or any other suitable format for storing or rendering such mechanical design structures). Similar to design structure 720, design structure 990 preferably comprises one or more files, data structures, or other computer-encoded data or instructions that reside on transmission or data storage media and that when processed by an ECAD system generate a logically or otherwise functionally equivalent form of one or more of the embodiments of the invention shown in FIGS. 1A, 1B, 2A-2H, 3A-3C, 4, and 5. In one embodiment, design structure 790 may comprise a compiled, executable HDL simulation model that functionally simulates the devices shown in FIGS. 1A, 1B, 2A-2H, 3A-3C, 4, and 5.

Design structure 790 may also employ a data format used for the exchange of layout data of integrated circuits and/or symbolic data format (e.g. information stored in a GDSII (GDS2), GL1, OASIS, map files, or any other suitable format for storing such design data structures). Design structure 790 may comprise information such as, for example, symbolic data, map files, test data files, design content files, manufacturing data, layout parameters, wires, levels of metal, vias, shapes, data for routing through the manufacturing line, and any other data required by a manufacturer or other designer/developer to produce a device or structure as described above and shown in FIGS. 1A, 1B, 2A-2H, 3A-3C, 4, and 5. Design structure 790 may then proceed to a stage 795 where, for example, design structure 790: proceeds to tape-out, is released to manufacturing, is released to a mask house, is sent to another design house, is sent back to the customer, etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the exemplary embodiments to the invention have been described, it will be understood that those skilled in the art, both now and in the future, may make various improvements and enhancements which fall within the scope of the claims which follow. These claims should be construed to maintain the proper protection for the invention first described.

What is claimed is:

1. A method for fabricating an apparatus by applying piezoelectric material for controlling a polymer through a nanopore, comprising:
    forming a reservoir filled with conductive fluid;
    forming a membrane, wherein the membrane separates the reservoir;
    forming a nanopore through the membrane;
    wherein the membrane comprises electrically conductive layers, piezoelectric layers, and electrically insulating layers; and
    wherein the piezoelectric layers are operative to control a size of the nanopore when a voltage is applied to the piezoelectric layers.

2. The method of claim 1, wherein the piezoelectric layers are operative to control the thickness of part of the membrane when a voltage is applied to the piezoelectric layers.

3. The method of claim 1, wherein the piezoelectric layers are operative to control a polymer through the nanopore when a voltage is applied to the piezoelectric layers.

4. The method of claim 1, wherein the piezoelectric layers are operative to clamp a polymer in the nanopore when a voltage is applied to the piezoelectric layers.

5. The method of claim 1, wherein the piezoelectric layers are operative to stretch a polymer in the nanopore when a voltage is applied to the piezoelectric layers.

6. The method of claim 1, wherein the piezoelectric layers are operative to break a polymer in the nanopore when a voltage is applied to the piezoelectric layers.

7. The method of claim 1, wherein the piezoelectric layers are operative to clamp a polymer at two locations to break the polymer when a voltage is applied to the piezoelectric layers.

8. The method of claim 1, wherein the piezoelectric layers are operative to increase in thickness to move a piezoelectric-layer-clamped polymer through the nanopore when a voltage is applied to the piezoelectric layers.

9. The method of claim 8, wherein the polymer is charged or non-charged.

10. An apparatus for controlling a polymer with piezoelectric material through a nanopore, comprising:
    a reservoir filled with a conductive fluid;
    a membrane separating the reservoir, the membrane comprising electrical conductive layers, piezoelectric layers, and insulating layers; and
    a nanopore through the membrane;
    wherein the piezoelectric layers are operative to control a polymer through the nanopore when a voltage is applied to the piezoelectric layers.

11. The apparatus of claim 10, wherein the piezoelectric layers are operative to control the thickness of part of the membrane when a voltage is applied to the piezoelectric layers.

12. The apparatus of claim 10, wherein the piezoelectric layers are operative to clamp the polymer in the nanopore when a voltage is applied to the piezoelectric layers.

13. The apparatus of claim 10, wherein the piezoelectric layers are operative to stretch the polymer in the nanopore when a voltage is applied to the piezoelectric layers.

14. The apparatus of claim 10, wherein the piezoelectric layers are operative to break the polymer in the nanopore.

15. The apparatus of claim 10, wherein the polymer is charged or non-charged.

16. A system for controlling a polymer through a nanopore utilizing piezoelectric material, comprising:
    an apparatus comprising:
        a reservoir filled with a conductive fluid;
        a membrane separating the reservoir, the membrane comprising electrically conductive layers, piezoelectric layers, and electrically insulating layers; and
        a nanopore through the membrane; and
    a voltage bias;
    wherein when the voltage bias is applied to the piezoelectric layers, the piezoelectric layers are operative to control a polymer through the nanopore.

17. The system of claim 16, wherein when the voltage bias is applied to the piezoelectric layers, the piezoelectric layers are operative to control a thickness of the membrane.

18. The system of claim 16, wherein when the voltage bias is applied to the piezoelectric layers, the piezoelectric layers are operative to clamp a polymer in the nanopore.

19. The system of claim 16, wherein when the voltage bias is applied to the piezoelectric layers, the piezoelectric layers are operative to stretch a polymer in the nanopore.

20. The system of claim 16, wherein when the voltage bias is applied to the piezoelectric layers, the piezoelectric layers are operative to break the polymer at a specific location by clamping the polymer at two points.

21. A method for operating an apparatus including piezoelectric material for controlling a polymer through a nanopore, comprising:
    placing a polymer in an apparatus having a membrane separating the reservoir, the membrane comprising electrically conductive layers, piezoelectric layers, and electrically insulating layers, wherein a nanopore is formed through the membrane; and
    applying a voltage to the piezoelectric layers;
    wherein when the voltage is applied to the piezoelectric layers, the piezoelectric layers are operative to control a size of the nanopore.

22. The method of claim 21, wherein the piezoelectric layers are operative to control the thickness of part of the membrane when the voltage is applied to the piezoelectric layers.

23. The method of claim 21, wherein the piezoelectric layers are operative to control a piezoelectric-layer-clamped polymer through the nanopore when the voltage is applied to the piezoelectric layers.

24. The method of claim 21, wherein the piezoelectric layers are operative to clamp a polymer in the nanopore when the voltage is applied to the piezoelectric layers.

25. The method of claim 21, wherein the piezoelectric layers are operative to stretch a polymer in the nanopore when the voltage is applied to the piezoelectric layers.

* * * * *